(12) United States Patent
Ostrovsky et al.

(10) Patent No.: US 11,083,451 B2
(45) Date of Patent: Aug. 10, 2021

(54) TISSUE ANCHOR WITH INSERTION DEVICE

(71) Applicant: Boston Scientific Scimed, Inc., Maple Grove, MN (US)

(72) Inventors: Isaac Ostrovsky, Wellesley, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 566 days.

(21) Appl. No.: 14/202,661

(22) Filed: Mar. 10, 2014

(65) Prior Publication Data

US 2014/0257340 A1  Sep. 11, 2014

Related U.S. Application Data

(60) Provisional application No. 61/776,157, filed on Mar. 11, 2013.

(51) Int. Cl.
*A61B 17/068* (2006.01)
*A61B 17/064* (2006.01)

(52) U.S. Cl.
CPC .......... *A61B 17/068* (2013.01); *A61B 17/064* (2013.01)

(58) Field of Classification Search
CPC . A61B 17/068; A61B 17/064; A61B 17/0644; A61B 17/0401; A61B 17/105; A61B 2017/0417; A61B 2017/0419; A61B 2017/0647; A61B 2017/0641; A61B 2017/0437; A61B 2017/0409; A61B 17/0682–0686; A61B 17/08–083; A61B 17/122–1285; A61B 2017/00584; A61B 17/0487–2017/049
USPC ........ 606/139, 142, 143, 151, 232, 152–158
See application file for complete search history.

(56) References Cited

U.S. PATENT DOCUMENTS

| | | | |
|---|---|---|---|
| 3,875,648 A | 4/1975 | Bone | |
| 4,014,492 A * | 3/1977 | Rothfuss | A61B 17/0644 227/132 |
| 4,317,451 A * | 3/1982 | Cerwin | A61B 17/0644 227/19 |
| 4,548,202 A | 10/1985 | Duncan | |
| 4,705,040 A | 11/1987 | Mueller | |
| 4,741,336 A * | 5/1988 | Failla | A61B 17/0643 227/181.1 |
| 4,976,715 A | 12/1990 | Bays | |
| RE34,021 E | 8/1992 | Mueller | |
| 5,297,714 A * | 3/1994 | Kramer | A61B 17/0644 227/175.1 |
| 5,350,400 A * | 9/1994 | Esposito | A61B 17/0644 227/902 |

(Continued)

*Primary Examiner* — Tan-Uyen T Ho
*Assistant Examiner* — Charles M Wei
(74) *Attorney, Agent, or Firm* — Brake Hughes Bellermann LLP

(57) ABSTRACT

In one embodiment, a medical device includes a first arm portion, a second arm portion and a base portion. The first arm portion has an inner surface and an outer surface. The second arm portion has a tissue piercing portion at a distal end, an inner surface and an outer surface. The base portion extends between the first arm portion and the second arm portion. A distance between the inner surface of the first arm portion and the inner surface of the second arm portion defines a depth of penetration into a tissue of a patient.

18 Claims, 14 Drawing Sheets

(56) References Cited

U.S. PATENT DOCUMENTS

| | | | |
|---|---|---|---|
| 5,622,257 A * | 4/1997 | Deschenes | A41H 37/008 |
| | | | 206/338 |
| 5,824,008 A | 10/1998 | Bolduc | |
| 5,830,221 A | 11/1998 | Stein | |
| 6,296,656 B1 | 10/2001 | Bolduc | |
| 6,322,563 B1 * | 11/2001 | Cummings | A61B 17/064 |
| | | | 606/104 |
| 6,491,707 B2 | 12/2002 | Makower | |
| 6,716,226 B2 * | 4/2004 | Sixto, Jr. | A61B 17/122 |
| | | | 606/142 |
| 7,056,333 B2 | 6/2006 | Walshe | |
| 8,192,458 B2 | 6/2012 | Hart | |
| 8,282,670 B2 | 10/2012 | Shipp | |
| 8,728,119 B2 * | 5/2014 | Cummins | A61B 17/0644 |
| | | | 411/439 |
| 2004/0122474 A1 | 6/2004 | Gellman | |
| 2004/0193188 A1 * | 9/2004 | Francese | A61B 17/122 |
| | | | 606/151 |
| 2005/0288708 A1 * | 12/2005 | Kammerer | A61B 17/0644 |
| | | | 606/221 |
| 2006/0247643 A1 * | 11/2006 | Bhatnagar | A61B 17/0642 |
| | | | 606/75 |
| 2007/0162030 A1 | 7/2007 | Aranyi | |
| 2009/0281377 A1 | 11/2009 | Newell | |
| 2010/0268255 A1 | 10/2010 | Ostrovsky | |
| 2012/0029538 A1 | 2/2012 | Reeser | |
| 2012/0289980 A1 | 11/2012 | Ostrovsky | |
| 2012/0296345 A1 * | 11/2012 | Wack | A61B 17/0483 |
| | | | 606/139 |
| 2013/0079813 A1 | 3/2013 | Li | |

* cited by examiner

TISSUE ANCHOR WITH INSERTION DEVICE

CROSS REFERENCE TO RELATED APPLICATION

This application is a Nonprovisional of, and claims priority to, U.S. Patent Application No. 61/776,157, filed on Mar. 11, 2013, entitled "TISSUE ANCHOR WITH INSERTION DEVICE", which is incorporated by reference herein in its entirety.

TECHNICAL FIELD

This disclosure relates generally to medical devices and more particularly to medical devices that include fixation devices or tissue anchors.

BACKGROUND

A variety of medical procedures are performed to provide support to portions of a body of a patient. For example, some medical procedures are performed to treat various female pelvic dysfunctions, including procedures to treat urinary incontinence, and correcting various prolapse conditions such as uterine prolapse, cystoceles, rectoceles, and vaginal vault prolapse.

Some such medical procedures include placing a support member or implant into the body of the patient such that the support member or implant provides support to a portion of the body of the patient. Specifically, in some medical procedures, the support member or implant may be fixed or coupled to the body of the patient at various locations within the body of the patient and a support portion of the support member or implant may be placed beneath the portion of the body to be supported. For instance, a patch of prosthetic material, such as a mesh material, may be attached to a layer (e.g., a thin layer) of tissues in the body of the patient such as a wall of an organ, for example, the vaginal wall. In some cases, a second portion of the mesh material may be attached to a layer of muscle or ligament on top of a bone such as, for example, the sacrum.

In some known medical procedures, tissue anchors or fixation devices are used fix or couple portions of the support member to portions of the body of the patient. A need exists for fixation devices or tissue anchors that effectively retain a support member in place within a body of a patient and to control a depth of penetration of the anchors. A need also exists for a tool for effectively placing such fixation or tissue anchors inside the body of the patient.

SUMMARY

In one general aspect, a medical device includes a first arm portion, a second arm portion and a base portion. The first arm portion has an inner surface and an outer surface. The second arm portion has a tissue piercing portion at a distal end, an inner surface and an outer surface. The base portion extends between the first arm portion and the second arm portion. A distance between the inner surface of the first arm portion and the inner surface of the second arm portion defines a depth of penetration into a tissue of a patient.

In another general aspect, a medical device includes an elongate member, a tack and a pusher. The elongate member defines a lumen. The elongate member has a cartridge at least partially disposed within the lumen. The cartridge has a ramp at a distal end. The tack has a first arm portion, a second arm portion and a base portion extending between the first arm portion and the second arm portion. The tack is disposed within the cartridge. The pusher is at least partially disposed within the lumen defined by the elongate member. The pusher is configured to engage the tack and move the tack from a position within the cartridge along the ramp at the distal end of the cartridge to a location outside of the cartridge.

In another general aspect, a method of placing a tack within a body of a patient includes (1) inserting a medical device within the body of the patient, the medical device includes an elongate member defining a lumen, the elongate member having a cartridge at least partially disposed within the lumen and the cartridge having a ramp at a distal end and a tack having a first arm portion, a second arm portion and a base portion extending between the first arm portion and the second arm portion, the tack being disposed within the cartridge and (2) moving the tack from a position within the cartridge along the ramp at the distal end of the cartridge to a location outside of the cartridge.

DETAILED DESCRIPTION

Figure 1:
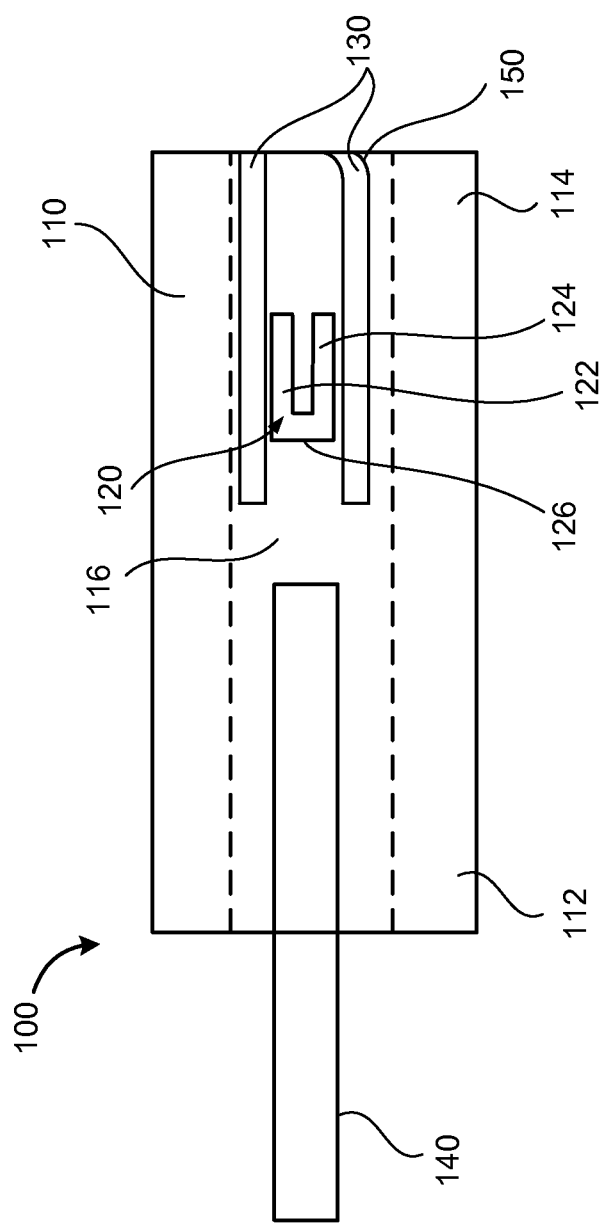
FIG. 1 is a schematic illustration of an apparatus according to an embodiment of the invention.

The devices and methods described herein are generally directed to procedures for placing implants within a body of a patient. In some embodiments, the implants are pelvic implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at any of several locations within the pelvic space to treat many different pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved.

Various fixation devices or tissue anchors or tacks, delivery devices, and methods are described for delivering and securing an implant within the body of the patient. The implants, fixation devices, delivery devices, and procedures described herein may be used in a female patient or a male patient.

An implant according to an embodiment of the invention can be implanted, for example, through an abdominal incision, in a retro-pubic direction (behind the pubic bone), or in a pre-pubic direction (in front of the pubic bone). In other embodiments, an implant can be placed in the direction of other anatomical structures or tissues as desired. A procedure to deploy a pelvic implant can include vaginal incisions, such as an anterior vaginal incision and/or an anterior vaginal incision. In some embodiments, a procedure may include an exterior incision.

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

FIG. 1 is a schematic illustration of an apparatus or medical device 100 according to an embodiment of the invention. The apparatus or medical device 100 includes an elongate member 110, a tack (or tissue anchor or fixation device) 120, and a cartridge 130. The illustrated embodiment also includes a pusher 140.

The apparatus 100 is configured to be inserted into a body of a patient such that at least a portion of the apparatus 100 is disposed within the body of the patient. As will be discussed in more detail below, the apparatus is configured to be placed adjacent a desired coupling or fixation location within the body.

The elongate member 110 includes a first end portion 112 and a second end portion 114. The elongate member 110 defines a lumen 116 (shown in dashed lines in FIG. 1). In some embodiments, the lumen 116 extends from the first end portion 112 to the second end portion 114. In some embodiments, the elongate member 110 defines an opening at the first end portion 112 and an opening at the second end portion 114 and the lumen 116 extends between the opening at the first end portion 112 and the opening at the second end portion 114. In other embodiments, the lumen only extends through a portion of the length of the elongate member 110. The lumen 116 is configured to receive and house various components of the apparatus 100 as will be described in detail below.

The tack (or tissue anchor or fixation device) 120 is configured to be placed within a body of a patient and to be fixedly coupled to a portion of the body of the patient. For example, in some embodiments, the tack 120 is configured to engage a bodily implant and be coupled to body tissue within the body of the patient to fixedly couple the implant to the body tissue.

In some embodiments, the tack (or tissue anchor or fixation device) 120 includes a first arm portion 122, a second arm portion 124, and a base portion 126 disposed between the first arm portion 122 and the second arm portion 124. The tack 120 is configured to enter a tissue of a patient to a specified depth. For example, a distance between the first arm portion 122 and the second arm portion 124 may define the specified depth. In this manner, the tack 120 is configured to control the depth of penetration into the tissue of the patient, where the tissue may be soft tissue or hard tissue. The tack 120 may be prevented from penetrating the tissue more than the specified depth as defined by the distance between the first arm portion 122 and the second arm portion 124.

In some embodiments, the tack 120 includes at least one tissue piercing portion. The tissue piercing portion is configured to pierce or be inserted into bodily tissue. In one embodiment, the tissue piercing portion may be at a distal end of the second arm portion 124. The tissue piercing portion may taper to a sharp point at the distal end of the second arm 124. In other embodiments, the tack 120 may include two tissue piercing portions. For example, the tissue piercing portions may be at distal ends of both the first arm portion 122 and the second arm portion 124.

In some embodiments, the tack 120 includes a elongated member at a distal end of the first arm portion 122, where the elongated member is perpendicular to or otherwise offset from an axis defined by the first arm portion 122, as illustrated and described in more detail below. The elongated member at the distal end of the first arm portion 122 may be configured to hold or at least assist in holding a bodily implant against the tissue of the patient. The elongated member at the distal end of the first arm portion 122 may be configured to prevent the tack 120 from penetrating deeper into the tissue of the patient. The elongated member at the distal end of the first arm portion 122 is configured to span across at least one opening of a bodily implant (e.g., at least one pore or opening of a mesh material) such that the tack 120 does not fall or pass through bodily implant further than desired.

In the illustrated embodiment, the apparatus 100 includes a cartridge 130. The cartridge 130 is at least partially disposed within the lumen 116. In some embodiments, the cartridge 130 may be fully disposed within the lumen 116. The cartridge 130 may include a ramp 150, which is illustrated in more detail in other figures described below. The ramp 150 may be curved upward or angled in a direction from the second arm portion 124 to the first arm portion 122 such that the ramp 150 has a curvature.

In some embodiments, the tack 120 is disposed within the cartridge 130. The second arm portion 124 of the tack 120 may include a nonplanar outer surface, where a curvature of the second arm portion 124 may match a curvature of the ramp 150. The cartridge 130 having the ramp 150 may be configured to guide and launch the tack 120 along the ramp 150 and into the tissue of patient. In this manner, the tack 120 may follow the curvature of the ramp 150 such that the tack 120 is angled into the tissue of the patient, even as the second end portion 114 (i.e., a distal end of the elongate member 110) is positioned flush against a bodily implant and/or tissue of the patient. The second arm portion 124, having the tissue piercing portion, may penetrate the tissue and the depth of penetration of the tack 120 may be limited as defined by the distance between the first arm portion 122 and the second arm portion 124.

In other embodiments (not illustrated), the apparatus may not include a cartridge 130 and the tack 120 may be disposed within the lumen 116 defined by the elongate member 110. The elongate member 110 may be configured with a nonplanar surface or ramp at a distal end that defines a curvature. In this manner, the tack 120 may follow the curvature of the ramp at the distal end of the elongate member 110 such that the tack 120 is angled into the tissue of the patient. The second arm portion 124, having the tissue piercing portion, may penetrate the tissue and the depth of penetration of the tack 120 may be limited as defined by the distance between the first arm portion 122 and the second arm portion 124.

In the illustrated embodiment, the apparatus 100 includes a pusher 140. The pusher 140 is configured to be disposed within the lumen 116 defined by the elongate member 110. For example, in some embodiments, the pusher 140 is configured to be disposed within the lumen 116 such that a portion of the pusher 140 is disposed within the lumen 116 and a portion of the pusher 140 is disposed outside of the lumen 116.

The pusher 140 is configured to move from a first location to a second location with respect to the elongate member 110. For example, in some embodiments, the pusher 140 is configured to move from a first location within the lumen 116 to a second location within the lumen 116 different than the first location. The pusher 140 is configured to contact the tack 120 while the tack 120 is disposed within the cartridge 130 and force the tack 120 out of the cartridge 130. For example, in some embodiments, when the pusher 140 is at its first position within the lumen 116 the pusher 140 does not contact the tack 120. As the pusher 140 is moved from its first position to its second position, the pusher 140 contacts the tack 120 and moves the tack 120 within the cartridge 130. In some embodiments, the pusher 140 is configured to expel or push the tack 120 to a location outside of the cartridge 130 when the pusher 140 is in its second position. The pusher 140 is configured to engage the tack 120 and move the tack 120 from a position within the cartridge 130 along the ramp 150 at the distal end of the cartridge 130 to a location outside of the cartridge 130.

In some embodiments, the apparatus 100 may include a handle and a trigger, which are illustrated and described below in more detail. The trigger may be configured to interact with the pusher 140 and to cause the pusher 140 to move from the first position within the lumen 116 to the second position within the lumen 116.

In some embodiments, the cartridge 130 is configured to house or receive multiple tacks. In some embodiments, the tacks may be disposed serially or end to end within the cartridge 130. In such embodiments, the pusher 140 may be configured to contact and move one of the tacks, which may in turn be configured to contact and move the other of the tacks.

In some embodiments, the cartridge 130 is configured to be removable from the apparatus 100 and replaced with a different cartridge (not illustrated). The cartridge 130 may be disconnected and removed from the apparatus 100 and another cartridge may be connected to the apparatus 100. A quick connect, quick disconnect type mechanism may be used to release one cartridge 130 from the apparatus 100 and secure another cartridge 130 to the apparatus 100. In this manner, one cartridge may include one type of tack 120 and the other cartridge may include another type of tack 120. For example, one cartridge 130 may include one or more tacks 120 made of one material and the other cartridge may include one or more tacks 120 made of another material. For example, in one embodiment, one cartridge 130 may include one or more tacks 120 made from a plastic material and the other cartridge may include one or more tacks made from a metal material. In this manner, the same apparatus 100 may be used with multiple cartridges having different types of tacks during a medical procedure that uses different types of tacks.

In other embodiments (not illustrated), the apparatus 100 may not include a cartridge 130 and the pusher 140 is configured to move from a first location within the lumen 116 to a second location within the lumen 116 different than the first location. The pusher 140 is configured to contact the tack 120 while the tack 120 is disposed within the lumen 116 defined by the elongate member 110 and force the tack 120 out of the elongate member 110. For example, in some embodiments, when the pusher 140 is at its first position within the lumen 116 the pusher 140 does not contact the tack 120. As the pusher 140 is moved from its first position to its second position, the pusher 140 contacts the tack 120 and moves the tack 120 within the lumen 116 defined by the elongate member 110. In some embodiments, the pusher 140 is configured to expel or push the tack 120 to a location outside of the elongate member 110 when the pusher 140 is in its second position. The pusher 140 is configured to engage the tack 120 and move the tack 120 from a position within the elongate member 110 along a ramp in the elongate member 110 at the distal end of the elongate member 110 to a location outside of the elongate member 110.

In some embodiments, the lumen 116 defined by the elongate member 110 is configured to house or receive multiple tacks. In some embodiments, the tacks may be disposed serially or end to end within the lumen 116 defined by the elongate member 110. In such embodiments, the pusher 140 may be configured to contact and move one of the tacks, which may in turn be configured to contact and move the other of the tacks.

In use, a tack 120 may be disposed within the cartridge 130, which may be disposed within the lumen 116 defined by the elongate member 110. The cartridge 130 may include a ramp 150 at a distal end, along which the tack 120 may move. The apparatus 100 may then be inserted into a body of a patient. For example, in some implementations, the apparatus 100 may be inserted into a body of a patient through an abdominal incision. In other implementations, the apparatus may be inserted into a body of a patient through a vaginal incision. An end portion, such as the second end portion 114 (a distal end portion) of the elongate member 110 may be disposed adjacent to the bodily tissue into which the tack 120 is to be inserted. In some embodiments, a bodily implant, such as a mesh type bodily implant, may be disposed between the second end portion 114 of the elongate member 110 and the tissue.

The pusher 140 may then be moved with respect to the elongate member 110 within the lumen 116 defined by the elongate member 110. For example, the pusher 140 may be moved from a first position to a second position. As the pusher 140 is moved from its first position or location within the lumen 116 to its second position or location within the lumen 116, the pusher 140 contacts and moves the tack 120 from a location within the cartridge 130 along the ramp 150 to a location outside of the cartridge 130.

In some embodiments, as the tack 120 is moved to a location or position outside of the cartridge 130, the tack 120 will pierce the bodily implant and the desired tissue. As the tack 120 moves along the ramp 150 to a location outside of the cartridge 130, the tack 120 may be angled by its movement along the ramp 150 so as to enter the desired tissue at an angle. Additionally, once the tack 120 is disposed outside of the cartridge (and away from the cartridge 130), the tack 120 may penetrate the tissue to a depth defined by a distance between a first arm portion 122 of the tack 120 and a second arm portion 124 of the tack 120. Accordingly, the tack 120 will be embedded within the bodily tissue and at least the second arm portion 124 will grasp or secure a portion of the bodily tissue to fixedly couple the tack 120 (and the bodily implant) to the bodily tissue. In some embodiments, the first arm portion 122 includes an elongated member at a distal end, where the elongated member is perpendicular to or otherwise offset from an axis defined by the first arm portion 122. The elongated member at the distal end of the first arm portion 122 is configured to hold at least a portion of the bodily implant to the bodily tissue and to further limit the depth at which the tack 120 can penetrate the bodily tissue.

In use, in other embodiments, the apparatus 100 may not include a cartridge and a tack 120 may be disposed within the lumen 116 defined by the elongate member 110. The elongate member 110 may include a ramp at a distal end, along which the tack 120 may move. The apparatus 100 may then be inserted into a body of a patient. For example, in some implementations, the apparatus 100 may be inserted into a body of a patient through an abdominal incision. In other implementations, the apparatus may be inserted into a body of a patient through a vaginal incision. An end portion, such as the second end portion 114 (a distal end portion) of the elongate member 110 may be disposed adjacent to the bodily tissue into which the tack 120 is to be inserted. In some embodiments, a bodily implant, such as a mesh type bodily implant, may be disposed between the second end portion 114 of the elongate member 110 and the tissue.

The pusher 140 may then be moved with respect to the elongate member 110 within the lumen 116 defined by the elongate member 110. For example, the pusher 140 may be moved from a first position to a second position. As the pusher 140 is moved from its first position or location within the lumen 116 to its second position or location within the lumen 116, the pusher 140 contacts and moves the tack 120 from a location within the lumen 116 along the ramp on the elongate member 110 to a location outside of the elongate member 110.

In some embodiments, as the tack 120 is moved to a location or position outside of the elongate member 110, the tack 120 will pierce the bodily implant and the desired tissue. As the tack 120 moves along the ramp on the elongate member 110 to a location outside of the elongate member 110, the tack 120 may be angled by its movement along the ramp so as to enter the desired tissue at an angle. Additionally, once the tack 120 is disposed outside of the elongate member 110, the tack 120 may penetrate the tissue to a depth defined by a distance between a first arm portion 122 of the tack 120 and a second arm portion 124 of the tack 120. Accordingly, the tack 120 will be embedded within the bodily tissue and at least the second arm portion 124 will grasp or secure a portion of the bodily tissue to fixedly couple the tack 120 (and the bodily implant) to the bodily tissue. In some embodiments, the first arm portion 122 includes an elongated member at a distal end, where the elongated member is perpendicular to or otherwise offset from an axis defined by the first arm portion 122. The elongated member at the distal end of the first arm portion 122 is configured to hold at least a portion of the bodily implant to the bodily tissue and to further limit the depth at which the tack 120 can penetrate the bodily tissue.

In some embodiments, the medical device includes a second tack. In such embodiments, the medical device may then be moved to another location within the body (and disposed adjacent different or another portion of bodily tissue). The second tack may then be inserted to such portion of bodily tissue.

Figure 2:
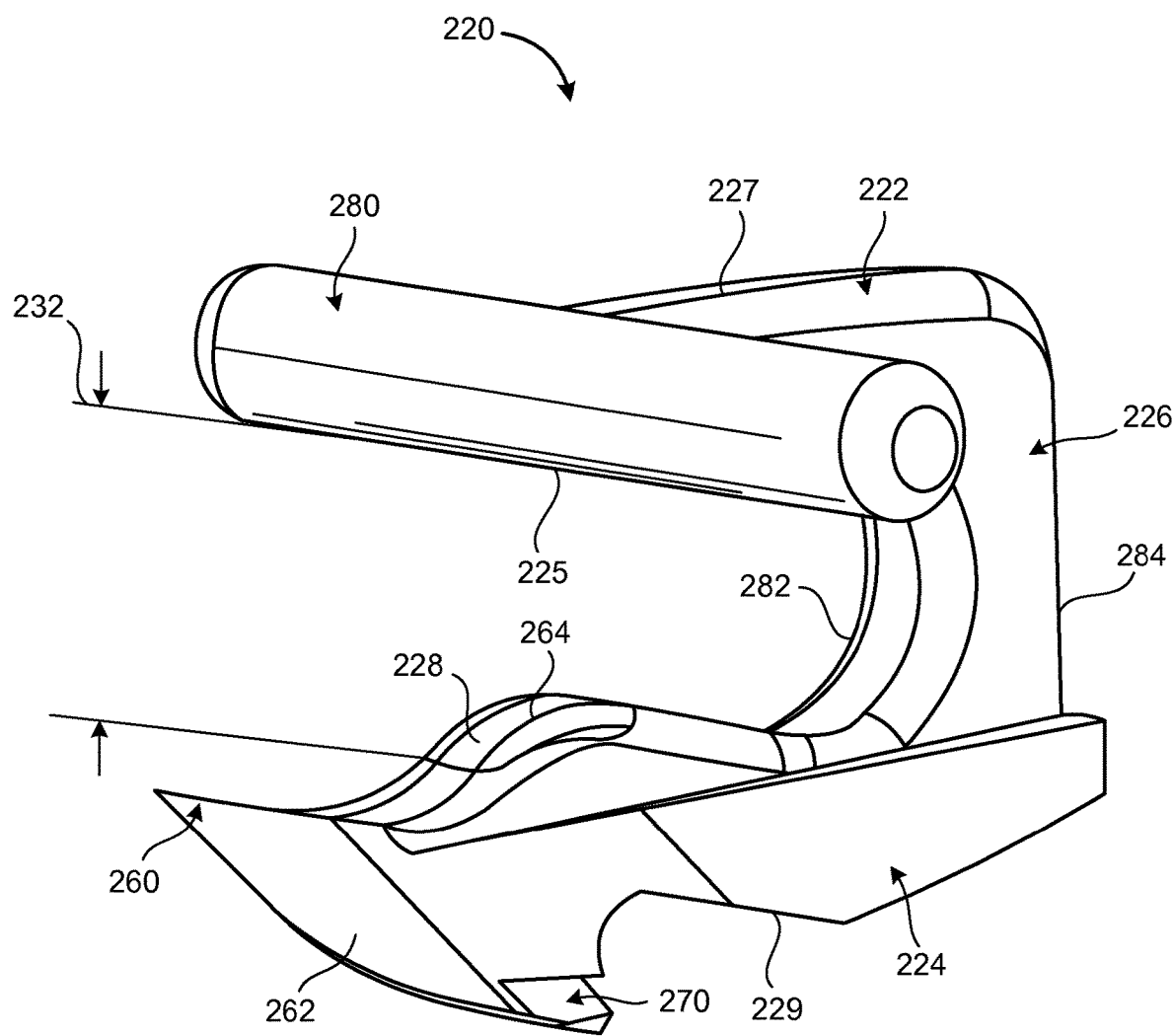
FIG. 2 is a perspective view of a tack according to an embodiment of the invention.
Figure 3:
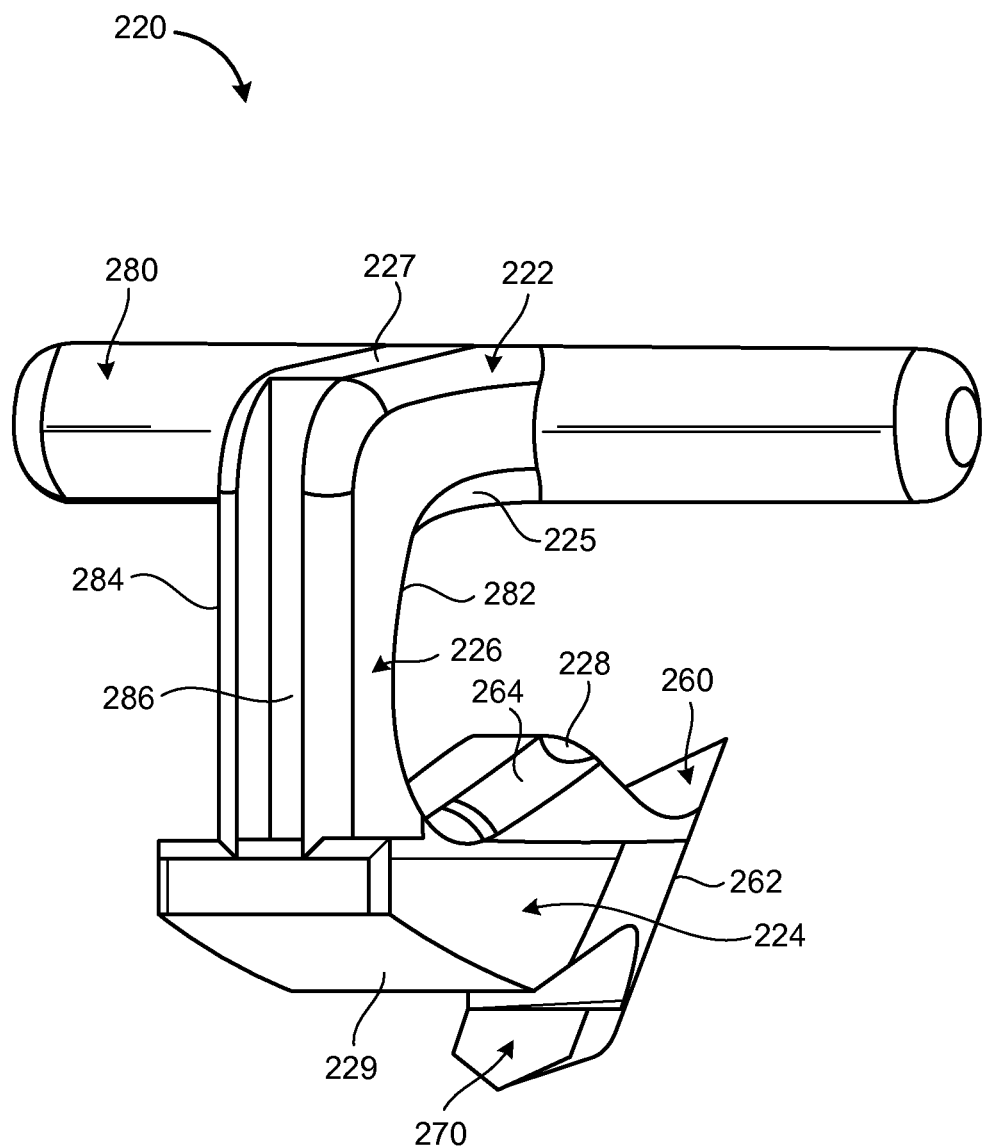
FIG. 3 is a perspective view of a tack according to an embodiment of the invention.

FIG. 2 is a perspective view of an apparatus or medical device or tack 220 according to an embodiment of the invention. FIG. 3 is a different perspective view of the tack 220 of FIG. 2. The tack (or tissue anchor or fixation device) 220 may include some or all of the features discussed above with respect to tack 120 of FIG. 1. The tack 220 is configured to be placed within a body of a patient and to be fixedly coupled to a portion of the body of the patient. For example, in some embodiments, the tack 220 is configured to engage a bodily implant and be coupled to body tissue within the body of the patient to fixedly couple the implant to the body tissue. The tack 220 may be used in both soft tissue and in hard tissue.

The tack 220 includes a first arm portion 222, second arm portion 224 and a base portion 226 disposed or extending between the first arm portion 222 and the second arm portion 224. The first arm portion 222 includes an inner surface 225 and an outer surface 227. The second arm portion 224 includes an inner surface 228 and an outer surface 229. A distance (or space) 232 is defined between the inner surface 225 of the first arm portion 222 and the inner surface 228 of the second arm portion 224. The distance 232 defines a depth of penetration into a tissue of a patient. The distance 232 is fixed between the inner surface 225 and the inner surface 228 such that the depth of penetration into the tissue is controlled. In this manner, a controllable depth of penetration into the tissue is achieved.

In one embodiment, the distance 232 may be between about 1 mm and 20 mm, which would correspond to a depth of penetration into the tissue between about 1 mm and 20 mm. In another embodiment, the distance 232 may be between about 1 mm and 10 mm, which would correspond to a depth of penetration into the tissue between about 1 mm and 10 mm. In other embodiments, the distance 232 may be different. In some embodiments, the distance 232 may be changed by changing a length of the base portion 226. In other embodiments, the distance 232 may be less than 1 mm, which would correspond to a depth of penetration into the tissue of less than 1 mm.

In the illustrated embodiment, the tack 220 is integrally or monolithically formed. In other words, the first arm portion 222, the second arm portion 224, and the base portion 226 are formed of a single piece of material. In other embodiments, the portions of the tack 220 are formed of separate pieces of material. In some such embodiments, the first arm portion 222 and the second arm portion 224 may be movably coupled to the base portion 226.

In the illustrated embodiment, the tack 220 includes a tissue piercing portion 260. The tissue piercing portion 260 is disposed at a distal end of the second arm portion 224 (opposite the base portion 226). The tissue piercing portion 260 is configured to pierce bodily tissue when the tack 220 is placed against or into bodily tissue.

In the illustrated embodiment, the inner surface 228 and the outer surface 229 of the second arm portion 224 may taper to a point to form or define the tissue piercing portion 260. The outer surface 229 at a distal end of the second arm portion 224 may curve upwards towards the inner surface 228 to form a curved portion 262 of the tissue piercing portion. The curved portion 262 has a curvature defined by the outer surface 229 sloping or curving towards the inner surface 228 that may match a curvature of the ramp 150 at the distal end of the cartridge 130 of FIG. 1, as further illustrated and described in more detail below. In embodiments without a cartridge, the curvature portion 262 may match a curvature of a ramp on the elongate member 110.

In the illustrated embodiment, the inner surface 228 of the second arm portion 224 is nonplanar. In one embodiment, the inner surface 228 that is nonplanar may define a sloped surface 264. The sloped surface 264 may be configured to assist in retaining the tack 220 in the bodily tissue. Additionally, surface 228 or 264 may have a barb, notch or the like facing towards base portion 226 to help secure the tack 220 in tissue. In this manner, the tissue piercing portion 260 pierces and penetrates the bodily tissue. As the tissue piercing portion 260 penetrates into the tissue, the sloped surface 264 also penetrates into the tissue and is configured to help prevent the tack 220 from backing out of the tissue.

In the illustrated embodiment, the outer surface 229 of the second arm portion 224 may be nonplanar. In one embodiment, the outer surface 229 that is nonplanar may be bow-shaped. The outer surface 229 may define a bow-shape by sloping or curving away from the base portion 226 downward to a point and then sloping or curving toward the tissue piercing portion 260 upward toward the inner surface 228.

In the illustrated embodiment, the tack 220 includes at least one barb 270. The barb 270 is configured as a back-looking barb. The point on the barb 270 faces in an opposite direction or nearly opposite direction from the point on the tissue piercing portion 260. The barb 270 is configured to anchor the tack 220 within the bodily tissue. In this manner, once the tissue piercing portion 260 pierces and penetrates the bodily tissue, the barb 270 follows the tissue piercing portion 260 into the tissue and then helps to anchor the tack 220 in the tissue. The barb 270 helps prevent the tack 220 from backing out of the tissue.

In the illustrated embodiment, the tack 220 includes an elongate member 280. The elongate member 280 is disposed at a distal end of the first arm portion 222 and defines an axis in a direction that is perpendicular or nearly perpendicular to an axis defined by the first arm portion 222. The elongate member 280 extends beyond the width of the first arm portion 222 on both sides of the first arm portion 222. The elongate member 280 may extend beyond the width of the first arm portion 222 in equal or near equal length. In one embodiment, the elongate member 280 is cylindrical-shaped. In other embodiments, the elongate member 280 may be other shapes, including flat, rectangular, triangular, etc. The elongate member 280 is configured to hold a bodily implant (e.g., prosthetic material) against the bodily tissue. The elongate member 280 also is configured to prevent the tissue piercing portion 260 from penetrating further into the bodily tissue. In this manner, for example, the elongate member 280 may span across a pore or opening in a bodily implant to prevent the tack 220 from penetrating further into the bodily tissue and to hold the bodily implant against the bodily tissue.

In the illustrated embodiment, the base portion 226 includes an inner surface 282 and an outer surface 284. The inner surface 282 of the base portion 226 is nonplanar and the outer surface 284 of the base portion 226 is planar or substantially planar. In other embodiments, the inner surface 282 may be planar or substantially planar and the outer surface 284 may be nonplanar or curved.

The outer surface 284 of the base portion 226 includes a slot 286. The slot 286 may extend along the length of the base portion 226 from the first arm portion 222 to the second arm portion 224. In other embodiments, the slot 286 may extend for a portion of the length of the base portion 226. The slot 286 is configured to protect the tissue piercing portion 260 from another tack 220 when multiple tacks are loaded in a cartridge. In this manner, the edges of the tissue piercing portion 260 from one tack 220 may push against the outer edges of the slot 286 and the point or sharp tip of the tissue piercing portion 260 may be disposed within the slot 286 without actually allowing the sharp tip to touch any part of the tack 220. When multiple tacks 220 are loaded in the apparatus 100, the tip on the tissue piercing portion 260 of one tack 220 is protected from breaking or dulling by the slot 286 of another tack 220.

Figure 4:
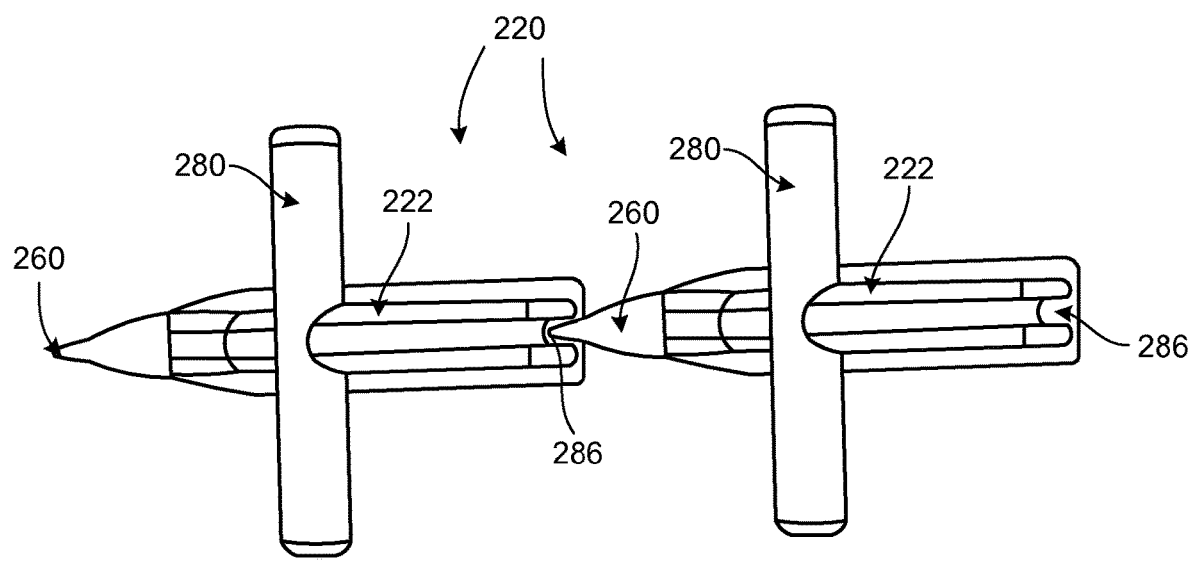
FIG. 4 is a top view of multiple tacks according to an embodiment of the invention.

Referring also to FIG. 4, a top view of multiple tacks 220 is illustrated. In this illustrated embodiment, two tacks 220 are illustrated as they may be disposed within a cartridge or in the lumen of the elongate member such that the tissue piercing portion 260 of one tack 220 aligns with and is disposed within the slot 286 of the tack 220 in front of it. The tissue piercing portion 260 is protected within the slot 286 because the sharp tip of the tissue piercing portion 260 may not touch any component of the tack 220 disposed in front of it.

In the illustrated embodiment, the edges of the tissue piercing portion 260 may be disposed on or rest on the outer edges of the slot 286 of the tack 220. The edges of the tissue piercing portion 260 may transmit the force from the one tack 220 to the other tack 220 within a cartridge or lumen of the elongate member to insert the tack 220 into a tissue of a patient.

Figure 5:
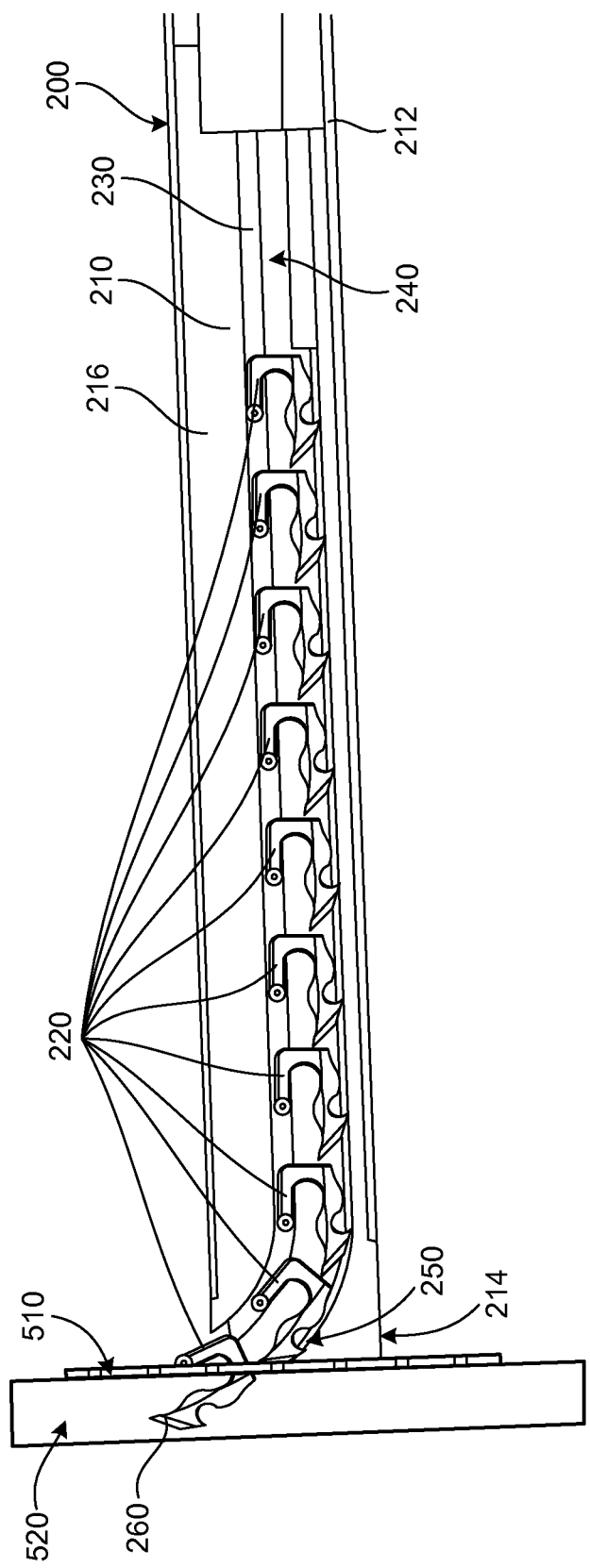
FIG. 5 is a break away side view of a portion of an apparatus according to an embodiment of the invention engaged with a bodily implant.
Figure 6:
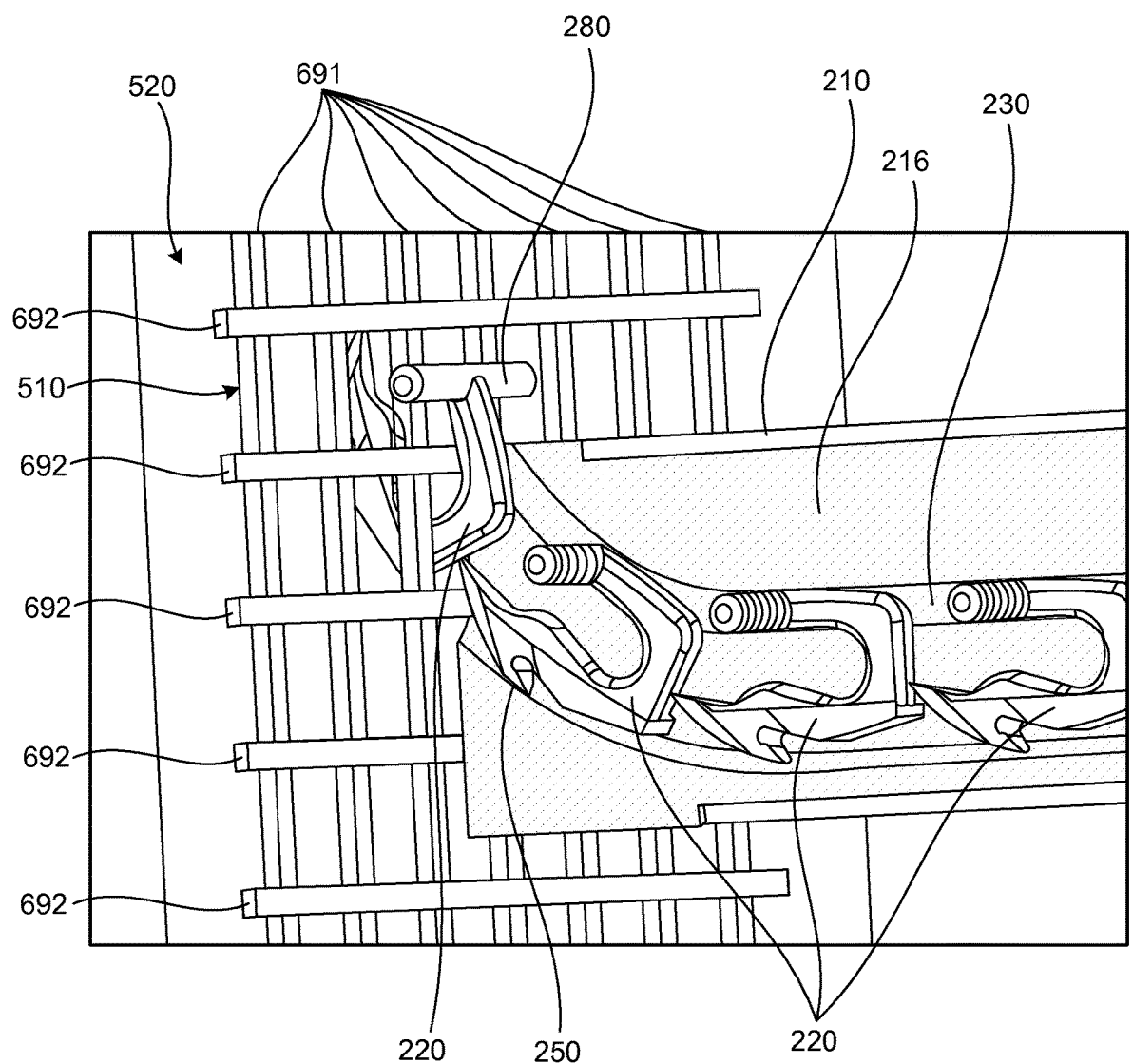
FIG. 6 is a break away side view of an apparatus according to an embodiment of the invention engaged with a bodily implant.

FIG. 5 is a break away side view of a portion of an apparatus 200 according to an embodiment of the invention engaged with a bodily implant. FIG. 6 is a detailed break away side view of a portion of the apparatus 200 according to an embodiment of the invention engaged with the bodily implant. The apparatus 200 may include some or all of the features of the apparatus 100 described above with respect to FIG. 1. The apparatus 200 includes an elongate member 210, a cartridge 230 having multiple tacks (or tissue anchors or fixation devices) 220 and a pusher 240.

The apparatus 200 is configured to be inserted into a body of a patient such that at least a portion of the apparatus 200 is disposed within the body of the patient. In some embodiments, the apparatus 200 is configured to be inserted into a body of a patient such that a distal end portion 214 of the elongate member 210 is disposed adjacent a desired coupling or fixation location within the body.

The elongate member 210 includes a first or proximal end portion 212 and the second or distal end portion 214. The elongate member 210 defines a lumen 216. In the illustrated embodiment, the lumen 216 extends from the first end portion 212 to the second end portion 214. The lumen 216 is configured to receive and house a cartridge 230 having multiple tacks 220.

In one embodiment, the cartridge 230 may house a plurality of tacks 220 (e.g., 1 to 10 tacks 220). In other embodiments, the cartridge 230 may house a different number of tacks 220. In the illustrated embodiment, the cartridge 230 includes 10 tacks 220. The tacks 220 are disposed within the cartridge 230 in an end to end relationship. Said another way, the distal end portion of one tack 220 is disposed adjacent a proximal end portion of another tack 220.

As discussed above, the tacks 220 are configured to be placed within a body of a patient and to be fixedly coupled to a portion of the body of the patient. For example, in the illustrated embodiment, the tacks 220 are configured to engage a bodily implant 510 and be coupled to bodily tissue 520 within the body of the patient to fixedly couple the implant 510 to the bodily tissue 520. In other embodiments, the tacks 220 are configured to couple a first bodily tissue portion to a second bodily tissue portion.

The cartridge 230 includes a ramp 250 at a distal end of the cartridge 230. The ramp 250 is configured to launch the tacks 220 at an angle with respect to the bodily implant 510 and the bodily tissue 520. In use, a distal end 214 of the apparatus 200 is placed flush against the bodily implant 510 and the bodily tissue 520. The tack 220 closest to the distal end 214 is moved along the ramp 250 from a first angle to a second angle, where the second angle is different from the first angle, and enters the bodily tissue 520 at the second angle to a depth of penetration defined by the distance between the inner surface on the first arm portion and the inner surface on the second arm portion.

In the illustrated embodiment, the bodily implant 510 is a mesh, sheet or other implant suitable for treating tissue disorders. The mesh includes multiple vertical strands 691 and multiple horizontal strands 692 that form the mesh and define multiple mesh openings or mesh pores. The tissue piercing portion 260 may penetrate through a mesh opening and into the bodily tissue 520. The elongate member 280 has a length that spans across at least two vertical strands 691. The tack 220 is prevented from penetrating deeper into the bodily tissue because the elongate member 280 is blocked by the vertical strands 691. In this manner, the elongate member 280 is configured to prevent further penetration into the bodily tissue 520. The elongate member 280 also assists in holding the bodily implant 510 in place against the bodily tissue 520.

The apparatus 200 includes a pusher 240. The pusher 240 is configured to be disposed within the lumen 216 defined by the elongate member 210. For example, the pusher 240 is configured to be disposed within the lumen 216 such that a portion of the pusher 240 is disposed within the lumen 216 and a portion of the pusher 240 is disposed outside of the lumen 216.

The pusher 240 is configured to move from a first location to a second location with respect to the elongate member 210. For example, in the illustrated embodiment, the pusher 240 is configured to move from a first location within the lumen 216 to a second location within the lumen 216 different than the first location. The pusher 240 is configured to contact one of the tacks 220 while the tacks 220 are disposed within the cartridge 230 and force the tack 220 at the distal end 214 out of the lumen 216 defined by the elongate member 210. When the pusher 240 is at its first position within the lumen 216 the pusher 240 may not contact the tacks 220. As the pusher 240 is moved from its first position to its second position, the pusher 240 contacts the tack 220 and moves the tack 220 within the cartridge 230. The pusher 240 is configured to expel or push the tack 220 to a location outside of the cartridge 230 when the pusher 240 is in its second position.

In the illustrated embodiment, each of the tacks 220 may be placed into bodily tissue. Specifically, each of the tacks 220 may be placed in different bodily tissue or different portions of bodily tissue. As the pusher 240 is advanced within the lumen 216 defined by the elongate member 210, the pusher 240 may contact and a first tack 220, which will contact and advance another tack 220, which will proceed in the same manner until the tack 220 nearest the distal end is launched up the ramp 250 to a location outside of the cartridge. The apparatus 200 may then be moved within the body of the patient (adjacent another portion of bodily tissue) and the pusher 240 may be moved to force another tack 220 to a location outside of the cartridge 230 and into the bodily tissue.

The illustrated embodiments illustrate the cartridge being separate from the elongate member. In such embodiments, the cartridge is disposed within the lumen of the elongate member and is coupled to the elongate member. In other embodiments, the cartridge is integrally or monolithically formed with the elongate member.

In some embodiments, the tacks 220 may be in a first configuration in the cartridge 230 and a second configuration when moved outside of the cartridge 230 and implanted in the bodily tissue. For example, the tacks 220 may be compressed in a low profile configuration when within the cartridge 230 (or the elongate member 210 if there is no cartridge) and then expand to a second configuration upon being moved outside of the cartridge 230 (or the elongate member 210 if there is no cartridge being used) and implanted in the bodily tissue. The second configuration may be a configuration that is a useful profile for implantation in the bodily tissue. In this manner, the configuration of the tacks 220 may change from a compressed or low profile configuration to an expanded or useful profile configuration when expelled or moved outside of the apparatus and into the bodily tissue.

Figure 7:
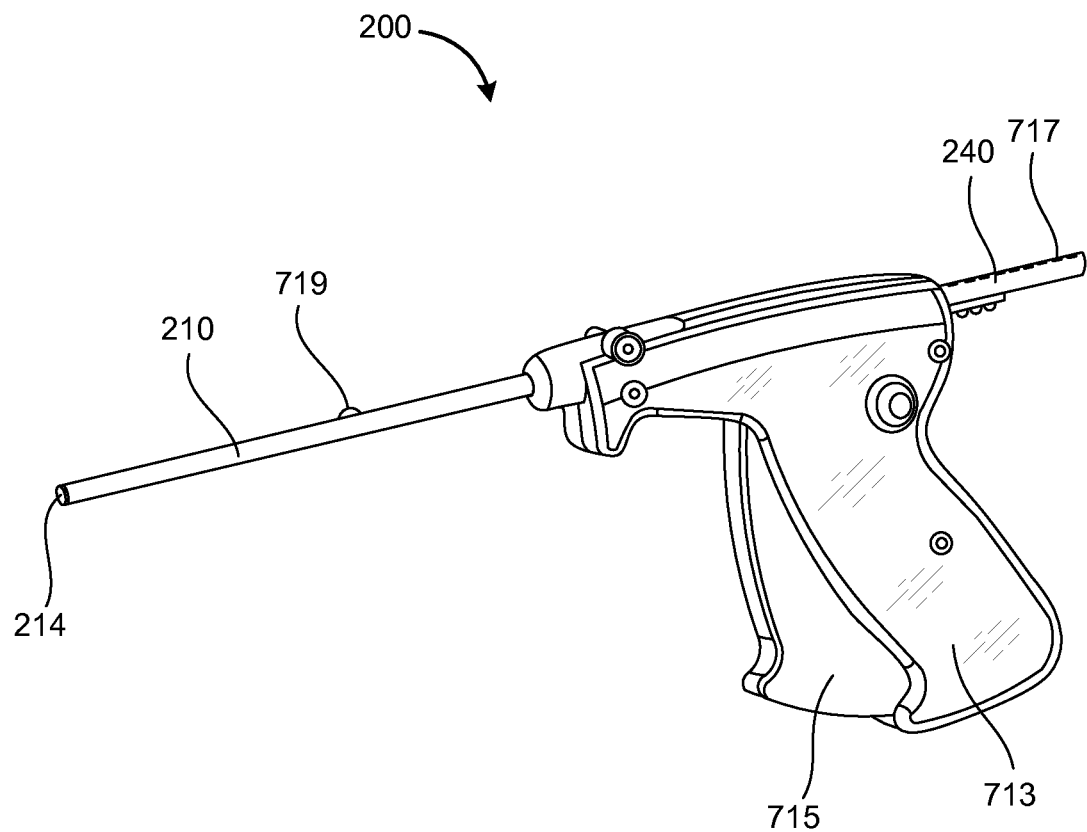
FIG. 7 is a perspective view of an apparatus according to an embodiment of the invention.

FIG. 7 is a perspective view of the apparatus 200 according to an example embodiment. In the illustrated embodiment, the apparatus 200 includes the elongate member 210 and the pusher 240. The apparatus 200 includes a handle 713, a trigger mechanism 715 and a cartridge lock 719. As discussed above, at least a portion of the apparatus 200 is configured to be inserted into a body of a patient. In one embodiment, the distal end 214 of the elongate member 210 is inserted into the body of the patient.

The handle 713 is configured to hold or house the elongate member 210. The handle 713 provides a grip area and holding point for the physician to hold the apparatus 200 when inserting the apparatus 200 into the patient. The handle 713 may be shaped and sized to enable the physician to comfortably grip and hold the apparatus 200 steady during use.

The trigger 715 is configured to interact with the pusher 240. Upon activation, the trigger 715 is configured to cause the pusher 240 to move from a first position to a second position within the lumen defined by the elongate member 210. The trigger 715 may move the pusher 240 in defined increments within the lumen of the elongate member 210. In the illustrated embodiment, the pusher 240 may include notches 717 that interact with the trigger 715 to advance the pusher 240 in increments defined by the spacing of the notches 717. The spacing of the notches 717 and the trigger 715 are configured to insert a single tack 220 into bodily tissue with a single pull of the trigger 715. Once a tack 220 is at a final position in the distal end of the cartridge 230, a single activation of the trigger 715 causes the tack 220 to move outside of the cartridge 230 along the ramp 250 and into the bodily tissue.

In the illustrated embodiment, the apparatus 200 also includes a cartridge lock button 719. The cartridge lock button 719 is configured to retain the cartridge 230 in position within the lumen 216 defined by the elongate member 210. The cartridge lock button 719 also may be configured to release the cartridge 230 from its position within the elongate member 210. The cartridge 230 may include a feature to interact with the cartridge lock button 719 that engages and disengages with the cartridge lock button 719 to secure and release the cartridge 230 within the elongate member 210.

Figure 8:
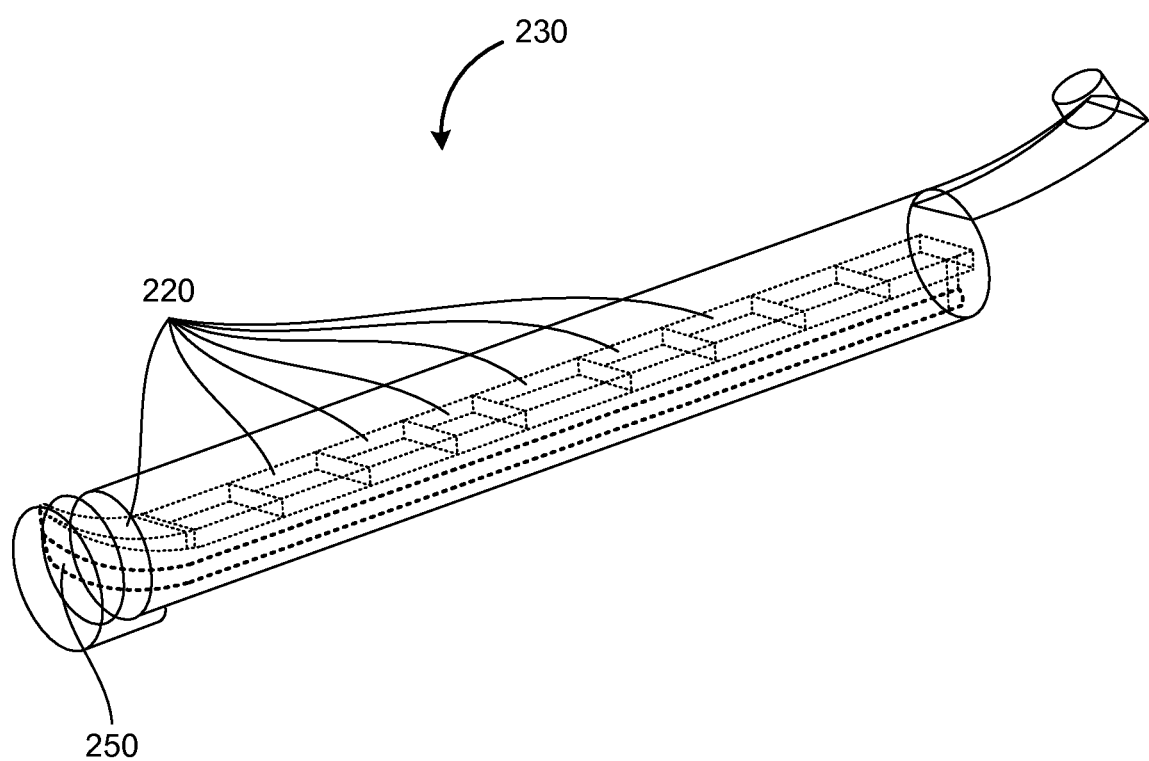
FIG. 8 is a break away perspective view of a portion of the apparatus of FIG. 7.

FIG. 8 is a break away perspective view of an example cartridge 230 having multiple tacks 220. The cartridge 230 includes a ramp 250 at the distal end. As discussed above, the ramp 250 is angled or curved such that the tacks 220 are expelled or launched at an angle into the bodily tissue of the patient.

In one embodiment, the cartridge 230 may be loaded with multiple tacks 220. The tacks 220 may be made of bio-compatible material(s). For example, the tacks 220 may be made of plastic such as, for instance, polypropylene or bio-absorbable plastic such polylactide. Other bio-compatible plastic materials may be used. The tacks 220 made of plastic may be used in procedures where the bodily tissue is soft tissue such as, for example, the vaginal wall.

In one embodiment, the tacks 220 may be made of bio-compatible metal materials such as titanium, nitinol, elgiloy or stainless steel. Other bio-compatible metal materials may be used. The tacks 220 made of metal may be used in procedures where the bodily tissue is hard tissue such as sacrum, where a thin layer of tough ligament covers the bone. In some embodiments, materials include ceramics or biologics (e.g., collagen, fibrin, elastin, extracellular matrix, etc.) In some embodiments, the tacks 220 comprise more than one material. In some embodiments, the tacks 220 comprise a biodegradable material. In some embodiments, the tacks 220 comprise at least one biodegradable material and at least one non-biodegradable material.

In some embodiments, the tacks 220 may be designed with the least amount of material necessary to function in order to have the least amount of irritation on bodily tissues when implanted. In some embodiments, the least amount of material may include one or more of the materials described above.

In some embodiments, the tacks 220 may comprise one or more coatings or other materials to improve the interaction with the bodily tissue at the implantation site. In some embodiments, the entire tack 220 may be coated with one or more such coatings or other materials. In some embodiments, a portion of the tack 220 may be coated with one or more such coatings or other materials.

In some embodiments, the tacks 220 may include one or more surface features to assist in retaining a location of the tack when implanted in bodily tissue. For example, the tacks 220 may include a roughness feature on one or more of the outer surfaces of the tack to assist in retaining the tack in a desired location and position when implanted in bodily tissue.

The apparatus 200 may use more than one cartridge 230 during the same procedure. For example, some procedures may use tacks 220 in both soft tissue and hard tissue during the same procedure. In use, the same apparatus 200 may be used with two different cartridges loaded with tacks made from different materials. A first cartridge loaded with tacks made of plastic may be used to penetrate soft tissue and a second cartridge loaded with tacks made of metal may be used to penetrate hard tissue. One example of such a procedure is a sacrocolpopexy procedure, where a bodily implant is attached in different places in different types of tissue. In some embodiments, the tacks 220 made of different materials are deployed from the same cartridge.

In some embodiments, a total number of tacks 220 needed for a particular procedure may be loaded into the cartridge 230 (or in the elongate member 210 if a cartridge is not used) at the time or just prior to the procedure. In other embodiments, the total number of tacks 220 may be pre-loaded prior to the procedure. In some embodiments, the cartridge 230 may be pre-loaded with a total number of tacks needed for a specific type of procedure.

In some embodiments, the tacks 220 may be loaded either from either end of the cartridge 230 (or elongate member 210), that is, the tacks 220 could be loaded from either the front or the back of the cartridge.

Figure 9:
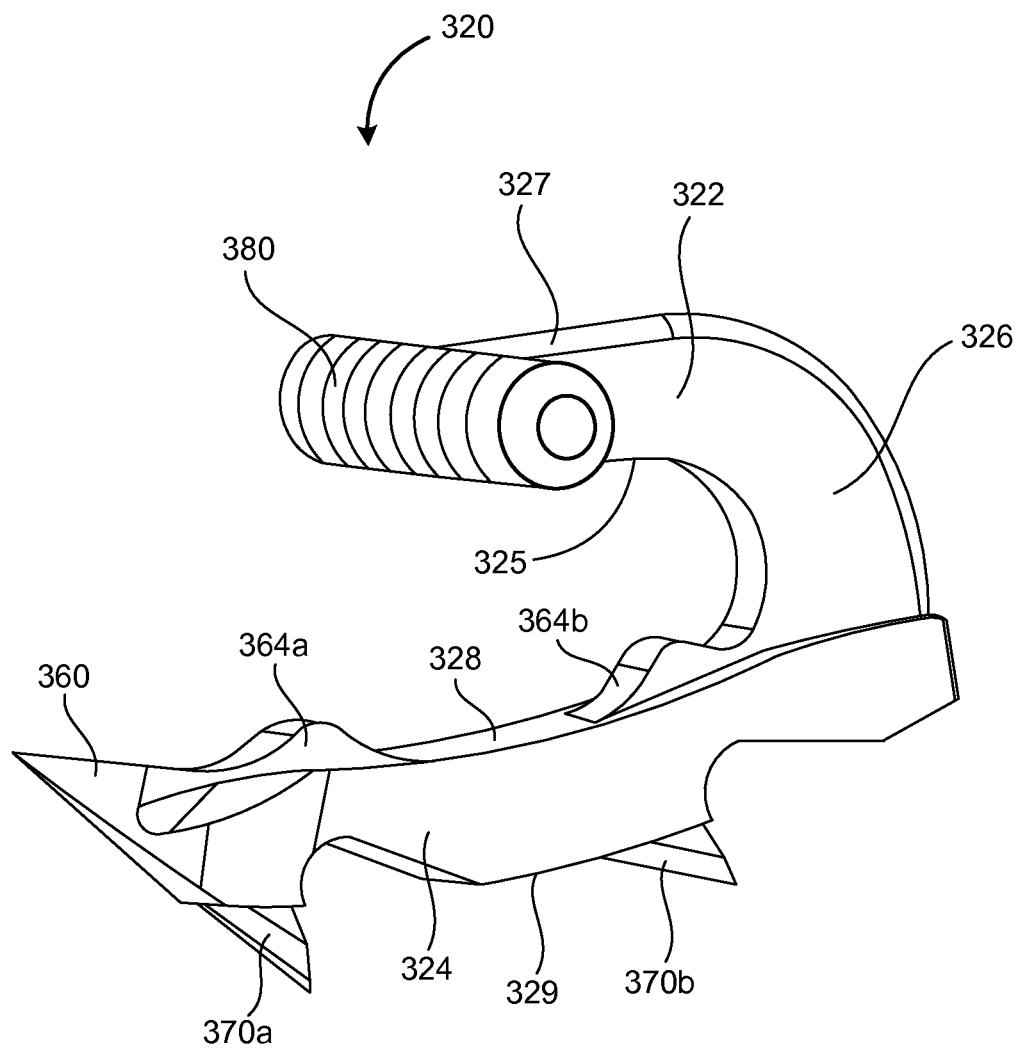
FIG. 9 is a perspective view of a tack according to an embodiment of the invention.

FIG. 9 is a perspective view of a tack 320 according to an example embodiment. The tack 320 includes a first arm portion 322, a second arm portion 324 and a base portion 326 extending between the first arm portion 322 and the second arm portion 324. The first arm portion 322 includes an elongate member 380 and the second arm portion includes a tissue piercing portion 360.

In the illustrated embodiment, the tack 320 is similar to the tack 220 illustrated and described above. The first arm portion 322 includes an inner surface 325 and an outer surface 327. The second arm portion 324 includes and inner surface 328 and an outer surface 329. The tack 320 includes two sloped surfaces 364a and 364b on the inner surface 328 of the second arm portion 324 and two barbs 370a and 370b on the outer surface 329 of the second arm portion 324. In this embodiment, the barbs 370a and 370b are backward-facing barbs.

The two barbs 370a and 370b are configured to anchor the tack 320 inside the bodily tissue after the tack 320 has pierced and penetrated the bodily tissue. The barbs 370a and 370b are configured to provide more longitudinal stability when transmitting force inside the cartridge of the apparatus. In the illustrated embodiment, the barbs 370a and 370b may not be identical and may have different lengths and/or may project at different angles with respect to the outer surface 329 of the second arm portion 324.

Figure 10:
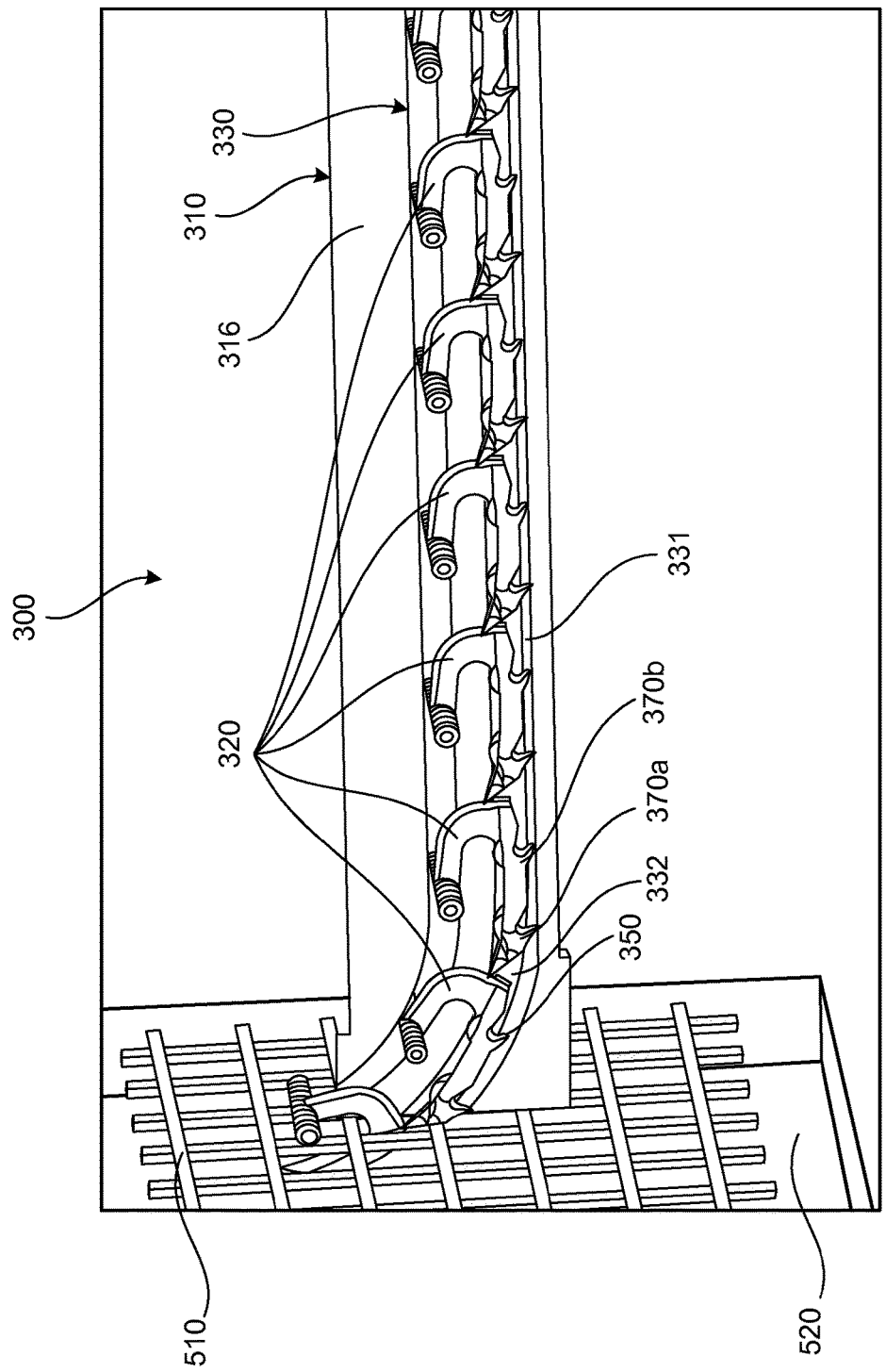
FIG. 10 is a break away side view of an apparatus according to an embodiment of the invention engaged with a bodily implant.

FIG. 10 is a break away side view of an apparatus 300 according to an example embodiment as engaged with a bodily implant 510 and bodily tissue 520. The apparatus 300 is the same or similar to the apparatus 100 and the apparatus 200 described and illustrated above. The apparatus 300 is configured to be inserted into a body of a patient. The apparatus 300 includes an elongated member 310 that defines a lumen 316. The apparatus 300 includes a cartridge 330 for carrying tacks 320, which include two barbs 370a and 370b.

In the illustrated embodiment, the cartridge 330 includes a first track 331 and a second track 332. The second track 332 defines the ramp 350. The barbs 370a and 370b on each tack 330 may be trimmed such that when the tack 320 sits on the barbs 370a and 370b on the first track 331, the longitudinal axis of the tack 320 is parallel to the longitudinal axis of the first track 331. In this manner, the pusher of apparatus 300 is also on the same longitudinal axis such that the force transmitted by the pusher is transmitted along the longitudinal axis.

As a tack 320 moves along the cartridge 330, the tack 320 first moves on the first track 331 and then onto the second track 332 at the distal end of the cartridge 330. When the tack 320 moves onto the second track 332, the tack 320 is supported on the second track 332 by the body of the second arm portion 324 and not by the barbs 370a and 370b. When the tack 320 is on the ramp 350, there is a clearance between the barbs 370a and 370b and the first track 331.

Figure 11:
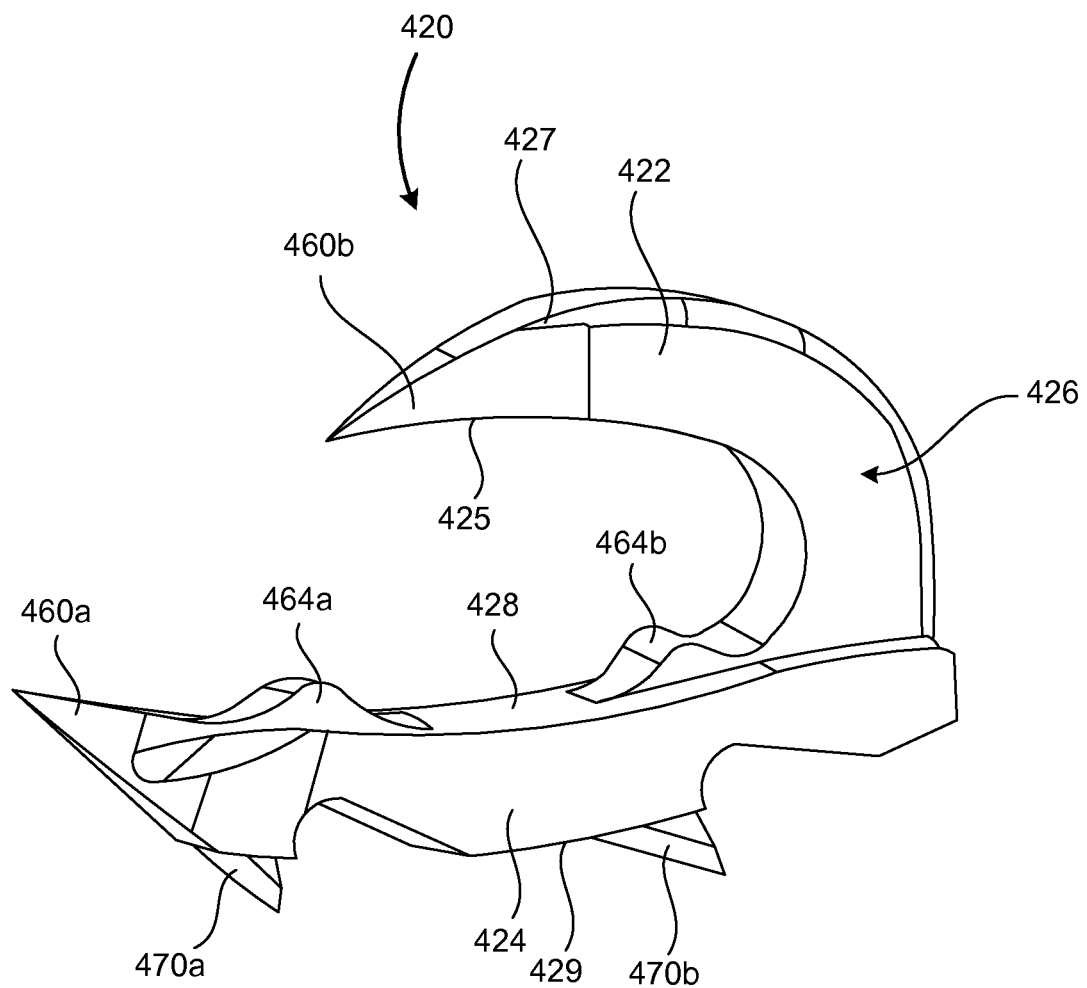
FIG. 11 is a perspective view of a tack according to an embodiment of the invention.

FIG. 11 is a perspective view of a tack 420 according to an example embodiment. The tack 420 includes a first arm portion 422, a second arm portion 424 and a base portion 426 extending between the first arm portion 422 and the second arm portion 424.

In the illustrated embodiment, the tack 420 is similar to the tack 320 illustrated and described above. The first arm portion 422 includes an inner surface 425 and an outer surface 427. The second arm portion 424 includes and inner surface 428 and an outer surface 429. The tack 420 includes two sloped surfaces 464a and 464b on the inner surface 428 of the second arm portion 424 and two barbs 470a and 470b on the outer surface 429 of the second arm portion 424. In this embodiment, the barbs 470a and 470b are backward-facing barbs.

The two barbs 470a and 470b are configured to anchor the tack 420 inside the bodily tissue after the tack 420 has pierced and penetrated the bodily tissue. The barbs 470a and 470b are configured to provide more longitudinal stability when transmitting force inside the cartridge of the apparatus. In the illustrated embodiment, the barbs 470a and 470b may not be identical and may have different lengths and/or may project at different angles with respect to the outer surface 429 of the second arm portion 424.

In the illustrated embodiment, the tack 420 does not include an elongate member on the first arm portion 422. In this embodiment, the tack 420 includes two tissue piercing portions. A first tissue piercing portion 460a is disposed on the distal end of the second arm portion 424 and a second tissue piercing portion 460b is disposed on the distal end of the first arm portion 422. The tack 420 is configured to securely catch one string or strand or wire of a bodily implant. For example, the tack 420 is configured to securely catch a wire from a neurotransmitter or cardio rhythm management device.

Figure 12:
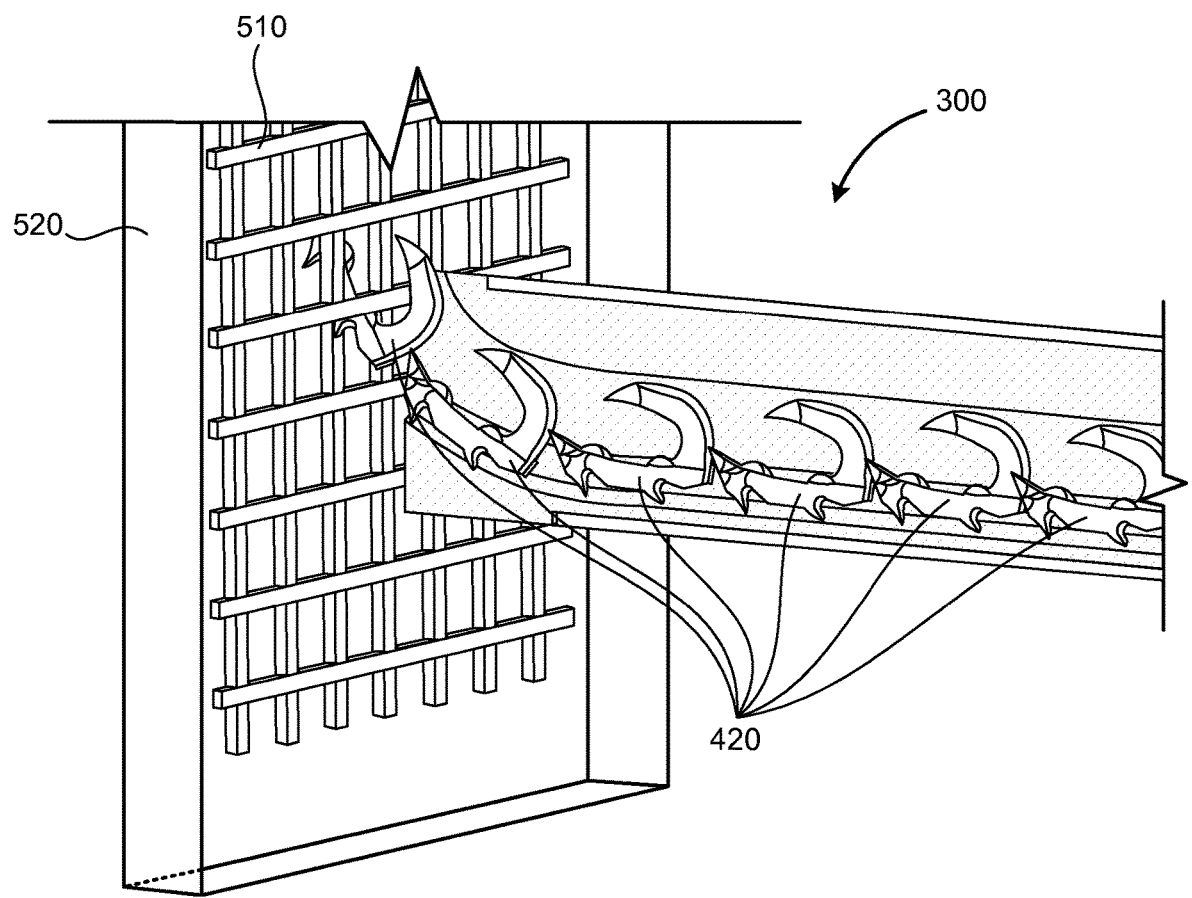
FIG. 12 is a break away side view of an apparatus according to an embodiment of the invention engaged with a bodily implant.

FIG. 12 is a break away side view of the apparatus 300 using tacks 420 engaged with a bodily implant in bodily tissue. In this embodiment, the tacks 420 are illustrated securing a bodily implant 510 to bodily tissue 520. The bodily implant 510 is a mesh with openings or pores.

Figure 13:
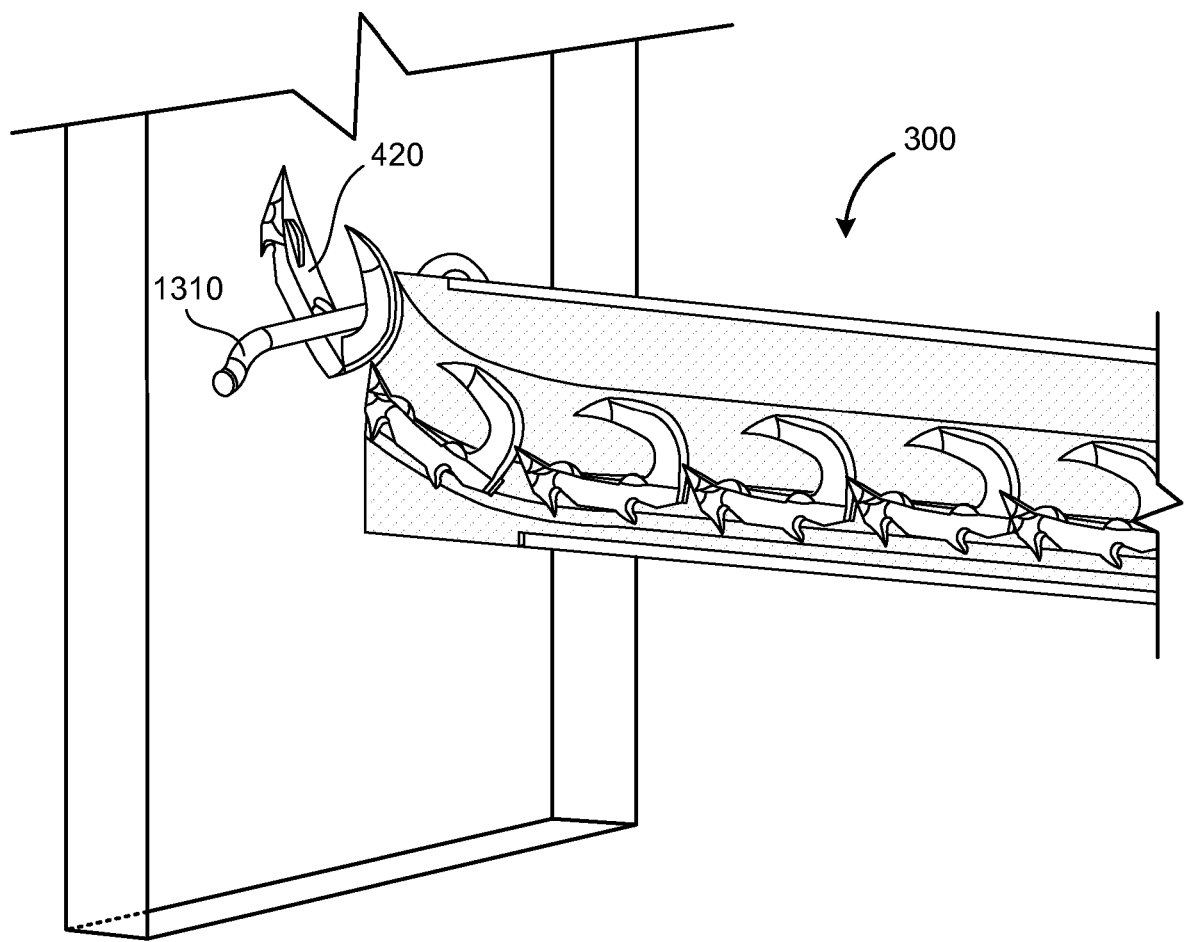
FIG. 13 is a break away side view of an apparatus according to an embodiment of the invention engaged with a bodily implant.

FIG. 13 is a break away side view of the apparatus 300 using tacks 420 engaged with a bodily implant in bodily tissue. In this embodiment, the tacks 420 are illustrated securing a bodily implant 1310 to bodily tissue 520. The bodily implant 1310 is a single string or wire.

Figure 14:
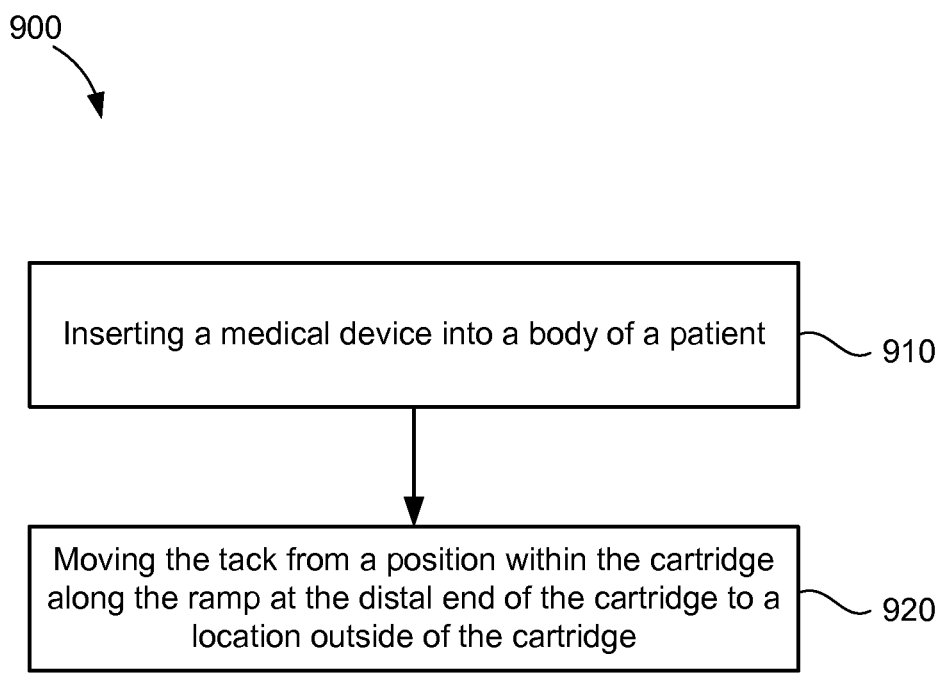
FIG. 14 is a flow chart of a method of placing an implant within a body of a patient according to an embodiment of the invention.

FIG. 14 is a flow chart of a method 900 of placing a tack within bodily tissue according to an embodiment of the invention. At 910, a medical device is inserted into a body of the patient. In some embodiments, the medical device includes an elongate member defining a lumen, a cartridge having a ramp disposed within the lumen and a tack disposed within the cartridge. At 920, the tack is moved from a position within the cartridge along the ramp at the distal end of the cartridge to a location outside of the cartridge. As the tack is moved along the ramp, the tack is angled from a first position to a second position such that the tack enters the bodily tissue at an angle. The tack angle may be defined by the angle of the ramp at the distal end of the cartridge. In embodiments where the medical device does not include a cartridge, the elongate member of the medical device may include a ramp along which the tack moves.

The medical device may deliver the tack to a fixed penetration depth, as defined by components of the tack. In this manner, as the tack enters the bodily tissue, the tack penetrates to a fixed depth and may be prevented from penetrating deeper into the tissue. In one example, the method and medical device may be used to secure a bodily implant (e.g., a mesh having mesh pores) to bodily tissue. The medical device may cause the tack to pierce through the mesh pores and the bodily tissue to a defined penetration depth and to secure the mesh against the bodily tissue. In this manner, one part of the tack may be on one side of the mesh penetrating into the bodily tissue and another part of the tack may be on the opposite side of the mesh holding the mesh against the bodily tissue.

In one embodiment, a medical device includes a first arm, a second arm portion and a base portion extending between the first arm portion and the second arm portion. The first arm portion has an inner surface and an outer surface. The second arm portion has a tissue piercing portion at a distal end, an inner surface and an outer surface. A distance between the inner surface of the first arm portion and the inner surface of the second arm portion defines a depth of penetration into a tissue of a patient.

In some embodiments, the distance between the inner surface of the first arm portion and the inner surface of the second arm portion is between about 1 mm and 10 mm.

In some embodiments, the first arm portion defines a first axis and includes an elongated member connected to a distal end of the first arm portion. The elongated member defines a second axis, where the second axis is substantially perpendicular to the first axis. In some embodiments, the elongated member is cylindrical-shaped.

In some embodiments, the second arm portion comprises at least one barb on the outer surface of the second arm portion and the inner surface of the second arm portion is nonplanar. In some embodiments, at least a portion of the inner surface of the second arm portion defines at least one ramp.

In some embodiments, the inner surface of the second arm portion and the outer surface of the second arm portion taper to a point to form the tissue piercing portion of the second arm portion. In some embodiments, the tissue piercing portion includes a curved portion at a distal end of the outer surface of the second arm portion. In some embodiments, the first arm portion includes a tissue piercing portion at a distal end of the first arm portion.

In some embodiments, the base portion includes an inner surface and an outer surface, the outer surface having a slot. In some embodiments, the base portion includes an inner surface and an outer surface, the inner surface being a nonplanar surface. In some embodiments, the inner surface of the based portion is concave.

In one embodiment, a medical device includes an elongate member defining a lumen, a tack and a pusher. The elongate member has a cartridge at least partially disposed within the lumen. The cartridge has a ramp at a distal end. The tack has a first arm portion, a second arm portion and a base portion extending between the first arm portion and the second arm portion. The tack is disposed within the cartridge. The pusher is at least partially disposed within the lumen defined by the elongate member. The pusher is configured to engage the tack and move the tack from a position within the cartridge along the ramp at the distal end of the cartridge to a location outside of the cartridge.

In some embodiments, the medical device includes a handle configured to hold the elongate member and a trigger configured to interact with the pusher and to cause the pusher to move from a first position within the lumen to a second position within the lumen, the first position within the lumen being different that the second position within the lumen.

In some embodiments, the medical device includes a plurality of the tacks disposed within the cartridge, where the base portion of the tacks includes an inner surface and an outer surface, the outer surface having a slot.

In some embodiments, the second arm portion of the tack includes an inner surface, an outer surface and a tissue piercing portion at a distal end of the second arm portion. The tissue piercing portion includes a curved portion at a distal end of the outer surface, the curved portion matching a curvature of the ramp of the cartridge.

In some embodiments, the first arm portion of the tack includes an inner surface and an outer surface and the second arm portion of the tack includes an inner surface and an outer surface, where a distance between the inner surface of the first arm portion and the inner surface of the second arm portion defines a depth of penetration into a tissue of a patient.

In one embodiment, a method of placing a tack within a body of a patient includes inserting a medical device within the body of the patient. The medical device includes an elongate member defining a lumen, the elongate member having a cartridge at least partially disposed within the lumen, the cartridge having a ramp at a distal end and a tack having a first arm portion, a second arm portion and a base portion extending between the first arm portion and the second arm portion, the tack being disposed within the cartridge. The method includes moving the tack from a position within the cartridge along the ramp at the distal end of the cartridge to a location outside of the cartridge.

In some embodiments, the moving includes engaging the tack with a pusher of the medical device.

In some embodiments, the first arm portion of the tack includes an inner surface and an outer surface and the second arm portion of the tack includes an inner surface and an outer surface, where a distance between the inner surface of the first arm portion and the inner surface of the second arm portion defines a depth of penetration into a tissue of a patient.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
   a first arm portion having an inner surface and an outer surface, the first arm portion having a proximal end portion and a distal end portion;
   a second arm portion having an inner surface and an outer surface, the second arm portion having a proximal end portion and a distal end portion, the distal end portion of the second arm portion defining a tissue piercing portion angled towards the first arm and configured to pierce a tissue of a patient and at least one barb configured to assist with preventing the medical device from backing out of the tissue, the at least one barb being defined by the outer surface of the second arm portion, the tissue piercing portion including a tip that extends in a first direction, the at least one barb including a tip that extends in a second direction opposite to the first direction, the first direction being disposed at a non-zero angle with respect to a longitudinal axis of the second arm portion, the inner surface of the second arm portion including a sloped protruded portion that protrudes in a direction towards the inner surface of the first arm portion, the sloped protruded portion configured to assist in retaining the medical device in the tissue of the patent; and
   a base portion extending along an axis between the proximal end portion of the first arm portion and the proximal end portion of the second arm portion, the base portion defining a slot extending parallel to the axis, the base portion having a mid-portion disposed between the proximal end portion of the first arm portion and the proximal end portion of the second arm portion, the mid-portion having an inner surface and an outer surface opposite the inner surface, wherein the outer surface is substantially planar and the inner surface is curved.

2. The medical device of claim 1, wherein a distance between the inner surface of the first arm portion and the inner surface of the second arm portion is between about 1 mm and 10 mm.

3. The medical device of claim 1, wherein the first arm portion defines a first central axis, the medical device including an elongated member connected to the distal end portion of the first arm portion, the base portion defining a second central axis, the elongated member defining a third central axis, wherein the third central axis is orthogonal to the first central axis, and the third central axis is orthogonal to the second central axis.

4. The medical device of claim 3, wherein the elongated member is cylindrical-shaped.

5. The medical device of claim 1, wherein the sloped protruded portion is disposed at a location on the inner surface of the second arm portion between the tissue piercing portion and the proximal end portion of the second arm portion.

6. The medical device of claim 1, wherein the inner surface of the second arm portion and the outer surface of the second arm portion taper to from the tip of the tissue piercing portion.

7. The medical device of claim 1, wherein the inner surface of the mid-portion of the base portion is concave.

8. The medical device of claim 1, wherein the slot is configured to receive a tissue piercing portion of another medical device.

9. A medical device, comprising:
   an elongate member having a sidewall defining a lumen, the elongate member having a cartridge at least partially disposed within the lumen, the cartridge having a proximal end portion and a distal end portion, the cartridge having a curved ramp at the distal end portion of the cartridge, the curved ramp having a curvature that curves away from a longitudinal axis of the cartridge, the curved ramp curving towards the sidewall of the elongate member;
   a tack having a first arm portion, a second arm portion and a base portion extending between the first arm portion and the second arm portion, the base portion having a mid-portion disposed between the proximal end portion of the first arm portion and the proximal end portion of the second arm portion, the mid-portion having an inner surface and an outer surface opposite the inner surface, wherein the outer surface is substantially planar and the inner surface is curved, the base portion including a slot that extends along a length of the base portion from the first arm portion to the second arm portion, the tack being disposed within the cartridge, the second arm portion of the tack including a proximal end portion and a distal end portion, the distal end portion of the second arm portion defining a tissue piercing portion angled towards the first arm portion and configured to pierce a tissue of a patient, a curved portion, and at least one barb configured to assist with preventing the medical device from backing out of the tissue, the curved portion having a curvature that matches the curvature of the curved ramp of the cartridge, the mid-portion of the tack defining a slot configured to receive a tissue piercing portion of another tack disposed within the cartridge; and a pusher at least partially disposed within the lumen defined by the elongate member, the pusher being configured to engage the tack and move the tack in a distal direction from a position within the cartridge along the curved ramp to a location outside of the cartridge such that the tack is launched at a non-zero angle with respect to the longitudinal axis of the cartridge.

10. The medical device of claim 9, further comprising:
a handle configured to hold the elongate member; and
a trigger configured to interact with the pusher and to cause the pusher to move from a first position within the lumen to a second position within the lumen, the first position within the lumen being different that the second position within the lumen.

11. The medical device of claim 9, further comprising a plurality of the tacks disposed within the cartridge.

12. The medical device of claim 9, wherein:
the first arm portion of the tack includes an inner surface and an outer surface; and
the second arm portion of the tack includes an inner surface and an outer surface, the inner surface of the second arm portion including the curved portion, the curved portion protruding in a direction towards the inner surface of the first arm portion, the curved portion configured to assist in retaining the medical device in the tissue of the patient.

13. The medical device of claim 9, wherein the tissue piercing portion includes a tip that extends in a first direction, the at least one barb including a tip that extends in a second direction opposite to the first direction, the first direction being disposed at a non-zero angle with respect to a longitudinal axis of the second arm portion.

14. The medical device of claim 9, wherein the mid-portion of the tack extends along an axis between the first arm portion and the second arm portion, the slot extending parallel to the axis.

15. A method of placing a tack within a body of a patient, comprising:
inserting a medical device within the body of the patient, the medical device including an elongate member having a sidewall defining a lumen, the elongate member having a cartridge at least partially disposed within the lumen, the cartridge having a proximal end portion and a distal end portion, the cartridge having a curved ramp at the distal end portion of the cartridge, the curved ramp having a curvature that curves away from a longitudinal axis of the cartridge, the curved ramp curving towards the sidewall of the elongate member, the cartridge including a tack having a first arm portion, a second arm portion, and a base portion extending along an axis between the first arm portion and the second arm portion, the base portion having a mid-portion disposed between the proximal end portion of the first arm portion and the proximal end portion of the second arm portion, the mid-portion having an inner surface and an outer surface opposite the inner surface, wherein the outer surface is substantially planar and the inner surface is curved, the base portion including a slot that extends parallel to the axis, the tack being disposed within the cartridge, the second arm portion of the tack including a proximal end portion and a distal end portion, the distal end portion of the second arm portion defining a tissue piercing portion angled towards the first arm portion and configured to pierce a tissue of a patient, a curved portion, and at least one barb configured to assist with preventing the medical device from backing out of the tissue, the curved portion having a curvature that matches the curvature of the curved ramp of the cartridge; and moving the tack from a position within the cartridge in a distal direction along the curved ramp to a location outside of the cartridge such that the tack is launched at a non-zero angle with respect to the longitudinal axis of the cartridge.

16. The method of claim 15, wherein the moving includes engaging the tack with a pusher of the medical device.

17. The method of claim 15, wherein:
the first arm portion of the tack includes an inner surface and an outer surface; and
the second arm portion of the tack includes an inner surface and an outer surface, the inner surface of the second arm portion including the curved portion, the curved portion protruding in a direction towards the inner surface of the first arm portion, the curved portion configured to assist in retaining the medical device in a tissue of a patient.

18. The method of claim 15, wherein the tissue piercing portion includes a tip that extends in a first direction, the at least one barb including a tip that extends in a second direction opposite to the first direction, the first direction being disposed at a non-zero angle with respect to a longitudinal axis of the second arm portion.

* * * * *